US00PP37851P2

(12) United States Plant Patent
Schoenmakers

(10) Patent No.: US PP37,851 P2
(45) Date of Patent: Nov. 24, 2026

(54) ***FITTONIA* PLANT NAMED 'KEJAPA114'**

(50) Latin Name: *Fittonia albivenis*
Varietal Denomination: KEJAPA114

(71) Applicant: Schoenmakers Tussenholding B.V., Haaren (NL)

(72) Inventor: Jan Cornelis Adrianus Maria Schoenmakers, Haaren (NL)

(73) Assignee: Schoenmakers Tussenholding B.V., Haaren (NL)

( * ) Notice: Subject to any disclaimer, the term of this patent is extended or adjusted under 35 U.S.C. 154(b) by 0 days.

(21) Appl. No.: 19/397,379

(22) Filed: Nov. 21, 2025

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

'KEJAPA114' is a new and distinctive *Fittonia* plant which is characterized by a compact, creeping growth habit, an abundance of oblanceolate to broadly elliptic foliage with strongly undulated margins, and an adaxial foliar surface that is colored with a bright pink-on-dark-green tessellated variegation pattern which further ages to a green-on-pink flecked variegation pattern. 'KEJAPA114' shows the stability of all these characteristics from generation to generation.

2 Drawing Sheets

Latin name of the genus and species:

The Latin name of the genus and species of the novel variety disclosed herein is *Fittonia verschaffeltii*, which is considered to be synonymous with *Fittonia albivenis*. (Verschaffeltii Group).

Variety denomination: The inventive variety of *Fittonia* plant disclosed herein has been given the variety denomination 'KEJAPA114'.

BACKGROUND OF THE INVENTION

Parentage: The claimed plant, 'KEJAPA114', originated as a naturally occurring partial-plant branch mutation of *Fittonia albivenis* 'Forest Flame' (U.S. Plant Pat. No. 16,897), which was discovered at a commercial greenhouse in Haaren, The Netherlands, in November 2005. The mutation was noted for its foliar pink-on-dark-green tessellated variegation pattern, which further ages to a green-on-pink flecked variegation pattern, relative to 'Forest Flame' which exhibits a red-on-very-dark-green tessellated variegation pattern. The mutation was harvested from the parent plant and subsequently propagated by rooting stem cuttings. The resulting plants were then grown to a mature size in order to evaluate and confirm the uniformity and stability of the unique characteristics first observed. Upon confirmation, in November 2006, the inventor selected the claimed *Fittonia* plant 'KEJAPA114'.

Asexual Reproduction: Asexual reproduction of 'KEJAPA114' by way of rooting stem cuttings, was first performed in November of 2005 at a commercial greenhouse in Haaren, The Netherlands. Through thirty-eight subsequent generations, the plants so produced have shown that the unique features of the instant cultivar are stable and reproduced true to type.

SUMMARY OF THE INVENTION

The cultivar 'KEJAPA114' has not been observed under all possible environmental conditions, and the phenotype may vary somewhat with variations in the instant environment such as temperature, day length, and light intensity, without, however, any variance in genotype. The following characteristics have been repeatedly observed and represent the distinguishing characteristics of the new *Fittonia* cultivar 'KEJAPA114'. These traits, in combination, distinguish 'KEJAPA114' as a new and distinct cultivar.

1. *Fittonia* 'KEJAPA114' exhibits a compact, creeping growth habit, with decumbent lateral branches, and an abundance of oblanceolate to broadly elliptic foliage with strongly undulated margins; and
2. *Fittonia* 'KEJAPA114' exhibits cross-venulate foliar venation, with light red veins on the adaxial surface, generally appearing as a pink coloration; and
3. *Fittonia* 'KEJAPA114' exhibits juvenile foliage with an upper leaf surface that is dark green with a light red coloration sharply bordering the entire network of veins, creating a prominent pink-on-dark-green tessellated variegation pattern; and
4. *Fittonia* 'KEJAPA114' exhibits mature foliage with an upper leaf surface that is centrally mid-green and darker green towards the margins, with veins that are broadly and diffusely margined with light red, creating a pink-on-dark-green tessellated variegation pattern which further ages to a green-on-pink flecked variegation pattern as the foliage ages and the light red coloration bordering the veins begins to coalesce.

BRIEF DESCRIPTION OF THE FIGURES

The photographs were taken using conventional techniques and although colors may appear different from actual colors due to light reflectance, it is as accurate as possible by conventional photographic techniques.

BOTANICAL DESCRIPTION OF THE PLANT

Figure 1:
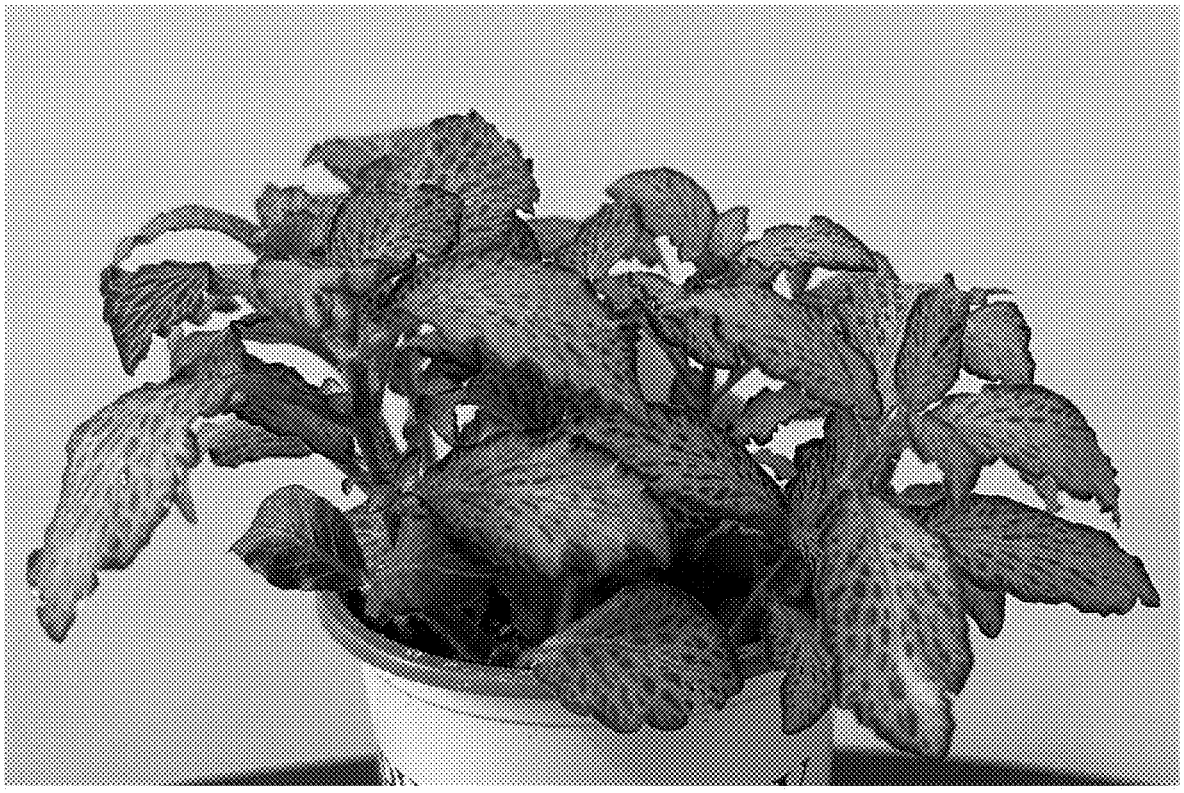
FIG. 1 shows, as nearly true as it is reasonably possible to make the same in color illustrations of this type, an exemplary plant of the new cultivar, 'KEJAPA114', approximately 14-weeks-old in a 350 mL nursery container. The plant shown was grown from a rooted cutting, potted into a nursery container, grown in a greenhouse in Stuarts Draft, Virginia.
Figure 2:
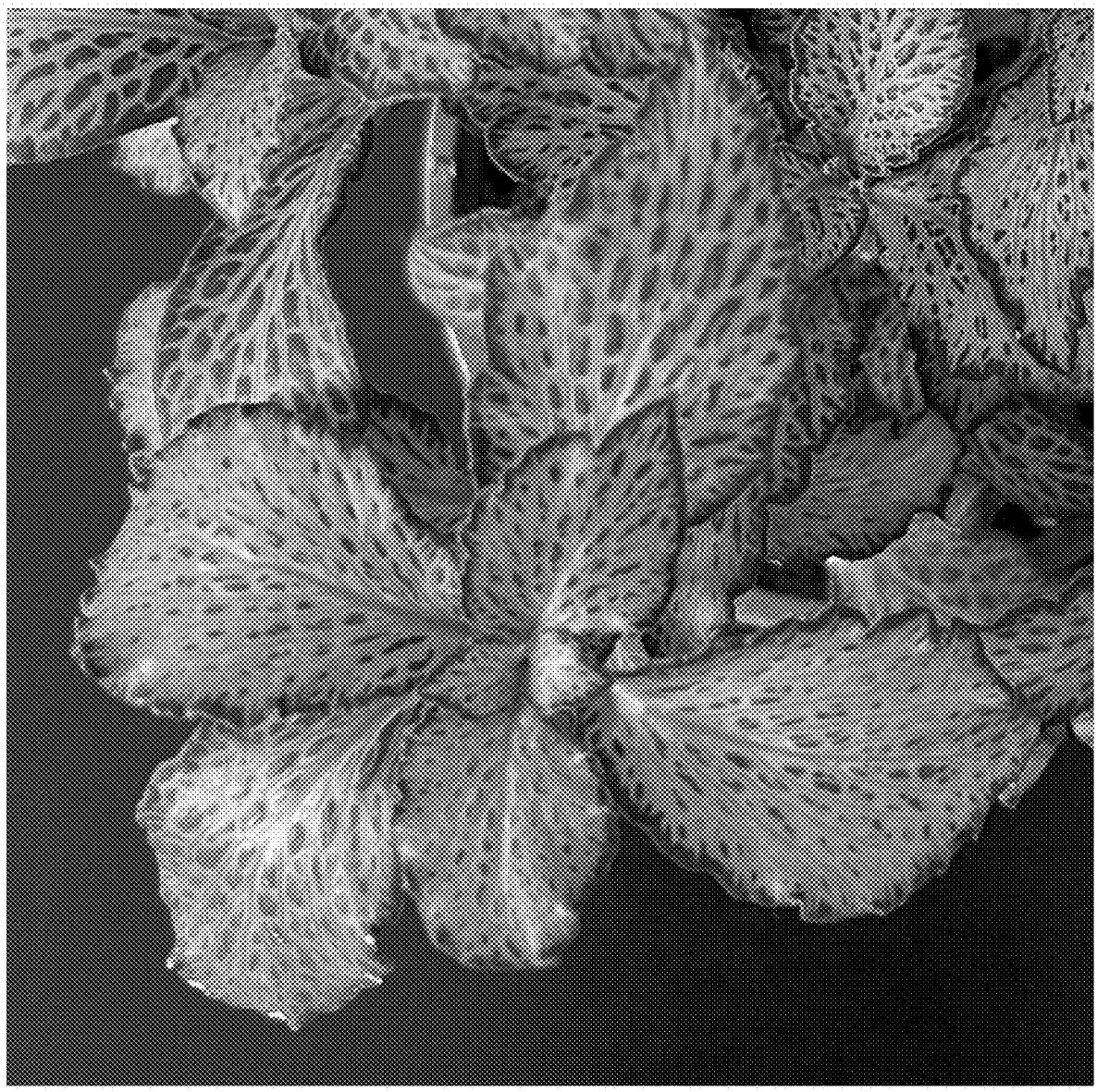
FIG. 2 illustrates the adaxial surface of the juvenile and mature foliage of the aforementioned 'KEJAPA114' plant.

The following observations and measurements were made in November of 2025. With the exception of the 51-week-old plants used to describe the stoloniferous habit of the plant, the *Fittonia* 'KEJAPA114' plants described in this botanical description are approximately 13-week-old grown in a 350 mL nursery container. Plants were produced using conventional greenhouse production protocols for *Fittonia* species which consisted of overhead irrigation once a week, grown under shade with light levels ranging from approximately 2,000 to 4,000 lumens, with ambient temperatures ranging from 20 to 35 degrees Celsius and humidity levels ranging from 60 to 95 percent. No pest or disease measures were employed. The 51-week-old plants were grown in the same manner as the aforementioned 13-week-old plants, only they were moved to an outdoor area with rain exclusion and 30 percent shade at 30-weeks-old. These plants were manually watered as needed, and no pest or disease control measures were employed.

Those skilled in the art will appreciate that certain characteristics will vary with older or, conversely, with younger plants. 'KEJAPA114' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, Second Edition.

A botanical description of 'KEJAPA114' and comparisons with the parent plant, sibling plants, and the most similar variety of common knowledge are provided below.

Plant description:

*Growth habit*.—Compact, creeping perennial.

*Average height*.—9.7 cm.

*Plant spread*.—18.7 cm.

*Propagation*.—Type — Asexual propagation is accomplished by way of rooting stem cuttings. Time to produce a rooted cutting — Approximately 4 weeks to produce a rooted cutting. Time to produce a rooted mature plant — Approximately 14 to 20 weeks grown in a 350 mL nursery container.

*Disease resistance*.—'KEJAPA114' exhibits susceptibility in common with the parent including bacterial leaf spot caused by *Xanthomonas campestris*, fungal blight caused by *Rhizoctonia solani*, as well as common arthropod pests such as aphids, moths, fungus gnats, and thrips.

*Environmental tolerances*.—Adapt to temperatures as high as 31 degrees Celsius. Thrives in partial shade with 60-70% humidity. Leaf scorch will occur in direct sunlight. 'KEJAPA114' requires irrigation once every 5-7 days and prefers growing under 50 $\mu mol/m^2/s$ shaded light.

Root system:

*General*.—Moderately dense, moderately branched rooting; roots are slightly fibrous.

*Distribution in the soil profile*.—Moderately deep.

*Diameter of roots*.—1.0 mm, on average.

*Texture*.—Smooth and glabrous.

*Color*.—Greyed-yellow, nearest to RHS 161D.

Stem:

*General branching habit*.—Basally branching main stems; with decumbent lateral branches that root at the nodes when in contact with the soil.

*Texture*.—Coriaceous; white, closest to 155A, trichomes present; approximately 0.7 mm in length.

*Luster*.—Glossy.

*Main stem*.—Length — 3.6 cm. Diameter — 0.2 cm. Internode length — 0.4 cm. Attitude — Upright. Texture — Coriaceous; white, closest to 155A, trichomes present; approximately 0.7 mm in length. Color of developing stems — Green, RHS 143C with a translucent overlay of greyed-purple, nearest to RHS 183D. Color of mature stems — Green, nearest to RHS 143C.

*Lateral branches*.—Length — 3.0 cm. Diameter — 0.3 cm. Internode length — 0.5 cm. Attitude — Laterally growing from the base of the plant. Cross-section — Terete. Texture — Coriaceous and pubescent, with white trichomes present, closest to RHS 155A; trichomes are approximately 0.7 mm in length. Color, adaxial and abaxial surfaces — Green, RHS 143C with a translucent overlay of greyed-purple, nearest to RHS 183D. Color at internodes — Green, RHS 143C.

Foliage:

*Quantity*.—6 leaves per lateral branch.

*Arrangement*.—Opposite.

*Attachment*.—Petiolate.

*Division*.—Simple.

*Lamina*.—Shape — Oblanceolate to broadly elliptic. Length — 4.4 cm. Width — 1.7 cm. Apex — Acute. Base — Cuneate. Aspect — Carinate. Attitude — Prostrate. Margin — Entire, highly undulated. Texture and luster of the adaxial surface — Coriaceous and matte with salient veins. Texture and luster of the abaxial surface — Coriaceous and matte with salient veins. Color — Juvenile foliage, adaxial surface — Green, RHS 131A, with the entire network of veins is sharply margined with red, a mixture of RHS 51D and 54D, creating a prominent pink-on-dark-green tessellated variegation pattern. Juvenile foliage, abaxial surface — Green, RHS 136C. Mature foliage, adaxial surface — Centrally colored mid-green, RHS 141A, and transitioning to a darker shade of green towards the margins, RHS 131A; the entire network of veins is broadly and diffusely margined with light red, a mixture of RHS 51D and 54D, creating a pink-on-dark-green tessellated variegation pattern. As the foliage ages, the pink coloration bordering the venation will begin to spread and nearly coalesce in the interveinal spaces which creates the effect of a green-on-pink flecked variegation pattern. Mature foliage, abaxial surface — Green, RHS 136C. Venation — Pattern — Cross-venulate. Color — Juvenile foliage, adaxial surface — Red, nearest to RHS 41A. Juvenile foliage, abaxial surface — Yellow-green, nearest to RHS 144D. Mature foliage, adaxial surface — Red, nearest to RHS 51A. Mature foliage, abaxial surface — Greyed-yellow, nearest to RHS 160D.

*Petiole*.—Length — 0.8 cm. Diameter — 0.2 cm. Strength — Strong. Texture — Coriaceous; trichomes present; white, closest to 155A, approximately 0.2 cm in length. Luster — Slightly glossy. Color, adaxial surface — Yellow-green, nearest to RHS 144C. Color, abaxial surface — Green, nearest to RHS 143C.

Inflorescence: No flowering has been observed to date.

COMPARISONS WITH THE PARENT PLANT

Plants of the new cultivar 'KEJAPA114' may be distinguished from the parent plant, *Fittonia albivenis* 'Forest Flame' (U.S. Plant Pat. No. 16,897), by the characteristics described in Table 1.

TABLE 1

Comparison Between KEJAPA114' and 'Forest Flame'

| Characteristic | 'KEJAPA114' | 'Forest Flame' |
|---|---|---|
| Plant size. | Smaller than 'Forest Flame'. | Larger than 'KEJAPA114'. |
| Abundance of lateral branches at 12-weeks-old. | Average of 6. | Average of 4. |
| Leaf shape and size. | Oblanceolate to broadly elliptic leaves with acute apices and cuneate bases. On average, 4.4 cm in length. | Narrow elliptic leaves with broad acute to rounded apices and attenuate bases. On average, 3.8 cm in length. |
| General coloration, adaxial surface of the mature foliage. | Centrally mid-green and darker green towards the margins, with veins that are broadly and diffusely margined with light red, creating a pink-on-dark-green tessellated variegation pattern, which further ages to a green-on-pink flecked variegation pattern as the foliage ages. | Very dark, darker than 'KEJAPA114', with veins that are broadly and diffusely margined with red, darker than 'KEJAPA114', creating a red-on-very-dark-green tessellated variegation pattern. |
| Venation color, adaxial surface. | Lighter red than 'Forest Flame', generally appearing as pink. | Darker shade of red relative to 'KEJAPA114'. |
| Venation color, abaxial surface. | Greyed-yellow, lighter and more yellow than 'Forest Flame'. | Yellow-green with greyed-orange near the base. |

COMPARISONS WITH THE MOST SIMILAR COMMERCIAL VARIETY

Plants of the new cultivar 'KEJAPA114' may be distinguished from the most similar commercial comparator known to the inventor, *Fittonia albivenis* 'Red Star' (U.S. Plant Pat. No. 18,047), by the characteristics described in Table 2.

TABLE 2

Comparison between 'KEJAPA114' and 'Red Star'

| Characteristic | 'KEJAPA114' | 'Red Star' |
|---|---|---|
| Leaf shape and size. | Oblanceolate to broadly elliptic leaves with acute apices and cuneate bases. On average, 4.4 cm in length. | Broad obovate to elliptic with average length of 4.9 cm and 3.1 cm in width. |
| Foliar margin undulation. | Less undulation than 'Red Star'. | More undulation than 'KEJAPA114'. |
| General coloration, adaxial surface of the mature foliage. | Centrally mid-green and darker green towards the margins, with veins that are broadly and diffusely margined with light red, creating a pink-on-dark-green tessellated variegation pattern, which further ages to a green-on-pink flecked variegation pattern as the foliage ages. | Green with broad margins of a lighter red than 'KEJAPA114' surrounding the venation. |
| Venation color, adaxial surface. | Lighter red than 'Red Star', generally appearing as a pink coloration. | Darker red than 'KEJAPA114', and appearing as a red coloration. |
| Venation color, abaxial surface. | Greyed-yellow, lighter and more yellow than 'Red Star'. | Yellow-green, greener than 'KEJAPA114'. |

Comparisons with sibling plants, 'KEJAPA123' (Co-pending U.S. Plant patent application Ser. No. 19/372,654), 'KEJAPA122' (Co-pending U.S. Plant patent application Ser. No. 19/375,831), 'KEJAPA113' (Co-pending U.S. Plant patent application Ser. No. 19/423,356), and 'KEJAPA115' (Co-pending U.S. Plant patent application Ser. No. 19/639,257). The new and distinct *Fittonia* plant, 'KEJAPA114', is distinguished from the sibling plants in producing an abundance of oblanceolate to broadly elliptic foliage with strongly undulated margins, and an adaxial foliar surface that is colored with a bright pink-on-dark-green tessellated variegation pattern which further ages to a green-on-pink flecked variegation pattern. 'KEJAPA123' produces an abundance of lanceolate foliage with strongly undulated margins, an adaxial foliar surface with green-white cross-venulate venation, and a dark green and white tessellate variegation pattern of the mature adaxial foliar surface. 'KEJAPA122' produces an abundance of narrow ovate to lanceolate foliage with serrulate margins that are highly undulated, and an adaxial foliar surface that is colored with a bright-red-on-dark-green, webbed variegation pattern. 'KEJAPA113' produces elliptic foliage with minutely crenulate and repand margins, and an adaxial foliar surface that is colored with a cerise-on-mid-green pinnately reticulate variegation pattern. 'KEJAPA115' produces broadly elliptic foliage with minutely crenulate margins, and an adaxial foliar surface that is colored with a bright-pink-on-dark-green pinnate variegation pattern.

That which is claimed is:

1. A new and distinct variety of *Fittonia* plant named 'KEJAPA114', substantially as described and illustrated herein.

* * * * *